US00PP08046P

United States Patent [19]

van der Knaap

[11] Patent Number: Plant 8,046

[45] Date of Patent: Nov. 24, 1992

[54] CHRYSANTHEMUM PLANT — COCARDE CULTIVAR

[75] Inventor: Jacques C. M. van der Knaap, De Lier, Netherlands

[73] Assignee: Fides Beheer B.V., De Lier, Netherlands

[21] Appl. No.: 679,659

[22] Filed: Apr. 2, 1991

[51] Int. Cl.[5] ..... A01H 5/00

[52] U.S. Cl. ..... Plt./74.1

[58] Field of Search ..... Plt./74, 74.1, 82.2, Plt./82.3, 82.4, 82.5

*Primary Examiner*—Howard J. Locker

*Attorney, Agent, or Firm*—Burns, Doane, Swecker & Mathis

[57] ABSTRACT

A new and distinct cultivar of Chrysanthemum plant name Cocarde is provided. The new cultivar was the result of a controlled breeding program wherein the Harlekijn cultivar (U.S. Plant Pat. No. 6,291) was pollinated by an unnamed plant designated 83.611. More specifically, the new cultivar forms attractive bicolored flowers wherein the ray florets are orange-red at the proximal end and yellow at the distal end and the disc florets exhibit a yellow-green appearance when mature. The inflorescence tends to be pyramidal in configuration. The response period of the flowers is approximately nine weeks. The new cultivar is particularly suited for use in the production of a cut single spray under greenhouse conditions.

1 Drawing Sheet

SUMMARY OF THE INVENTION

The present invention comprises a new and distinct cultivar of Chrysanthemum, botanically known as *Dendranthema morifolium* Ramat., previously, *Chrysanthemum morifolium,* Ramat., and hereinafter is referred to by the cultivar name Cocarde.

The new cultivar is the product of a planned breeding program which had as its objective the creation of a new Chrysanthemum cultivar which exhibits attractive red-yellow bicolored flowers, exhibits a flower response period of approximately nine weeks, and possesses the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1986 at De Lier, The Netherlands. The female parent (i.e., the seed parent) was the Harlekijn cultivar (U.S. Plant Pat. No. 6,291) and the male parent (i.e., the pollen parent) was an unnamed plant designated 83.611. The parentage of the new cultivar can be summarized as follows:

Harlekijn × 83.611.

The seeds resulting from the above pollination were sown and plantlets were obtained which were physically and biologically different from each other. Selective study resulted in the identification of a single plant of the new variety.

It was found that the new cultivar of the preesnt invention:

(a) exhibits attractive single flowers having an overall diameter of approximately 60 to 70 mm. wherein the ray florets are orange-red at the proximal end and yellow at the distal end and the disc is yellow-green when mature, (b) bears flowers in a somewhat pyramidal configuration, (c) exhibits a flower response period of approximately nine weeks, (d) forms attractive dark green foliage, and (e) has the ability to produce flowers of commercially acceptable quality throughout the year in a cut mum production program.

Asexual reproduction of the new cultivar by cuttings initially taken during September, 1986, as performed at De Lier, The Netherlands, in a controlled environment has demonstrated that the characteristics of the new cultivar as herein disclosed are firmly fixed and are retained through successive generations of asexual propagation.

Cocarde has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Pierrot cultivar (non-patented in the United States), it is observed that the flower size tends to be smaller, the bicolored ray florets exhibit a different color pattern, more vigor is exhibited, and the flower response tends to be slower. Otherwise, the color of the ray florets tends to be substantially the same in each instance.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is The R.H.S. Colour Chart of The Royal Horticultural Society, London, England. The color values were determined at 11:00 a.m. to 12:00 noon under natural daylight conditions at De Lier, The Netherlands, during October, 1989. The plants described were grown under standard greenhouse conditions which approximate those commonly utilized for the production of cut mums.

Classification:

*Botanical.*—*Dendranthema morifolium* Ramat., cv. Cocarde.

*Commercial.*—Cut single spray.

Inflorescence

A. Capitulum:

*Form.*—Pyramidal.

*Type.*—Single.

*Diameter across face.*—Approximately 60 to 70 mm. on average.

B. Corolla of ray and disc florets:

*Color (General tonality from a distance of three meters).*—Yellow.

*Color ray florets.*—(Top surface). — Bicolored having Orange-Red Group 34A at the proximal end and Yellow Group 9A at the distal end.

*Color disc florets.*—Yellow-Green Group 144A when mature.

C. Reproductive organs:

*Androecium.*—Present in disc florets.

*Gynoecium.*—Present in disc florets.

Plant

A. General Appearance:

*Height.*—Approximately 100 cm. on average.

B. Foliage:

*Color (upper surface).*—Yellow-Green Group 147A.

*Color (under surface).*—Yellow-Green Group 147B.

I claim:

1. A new and distinct cultivar of Chrysanthemum plant named Cocarde, substantially as herein shown and described, which:

(a) exhibits attractive single flowers having an overall diameter of approximately 60 to 70 mm. wherein the ray florets are orange-red at the proximal end and yellow at the distal end and the disc is yellow-green when mature, (b) bears flowers in a somewhat pyramidal configuration, (c) exhibits a flower response period of approximately nine weeks, (d) forms attractive dark green foliage, and (e) has the ability to produce flowers of commercially acceptable quality throughout the year in a cut mum production program.

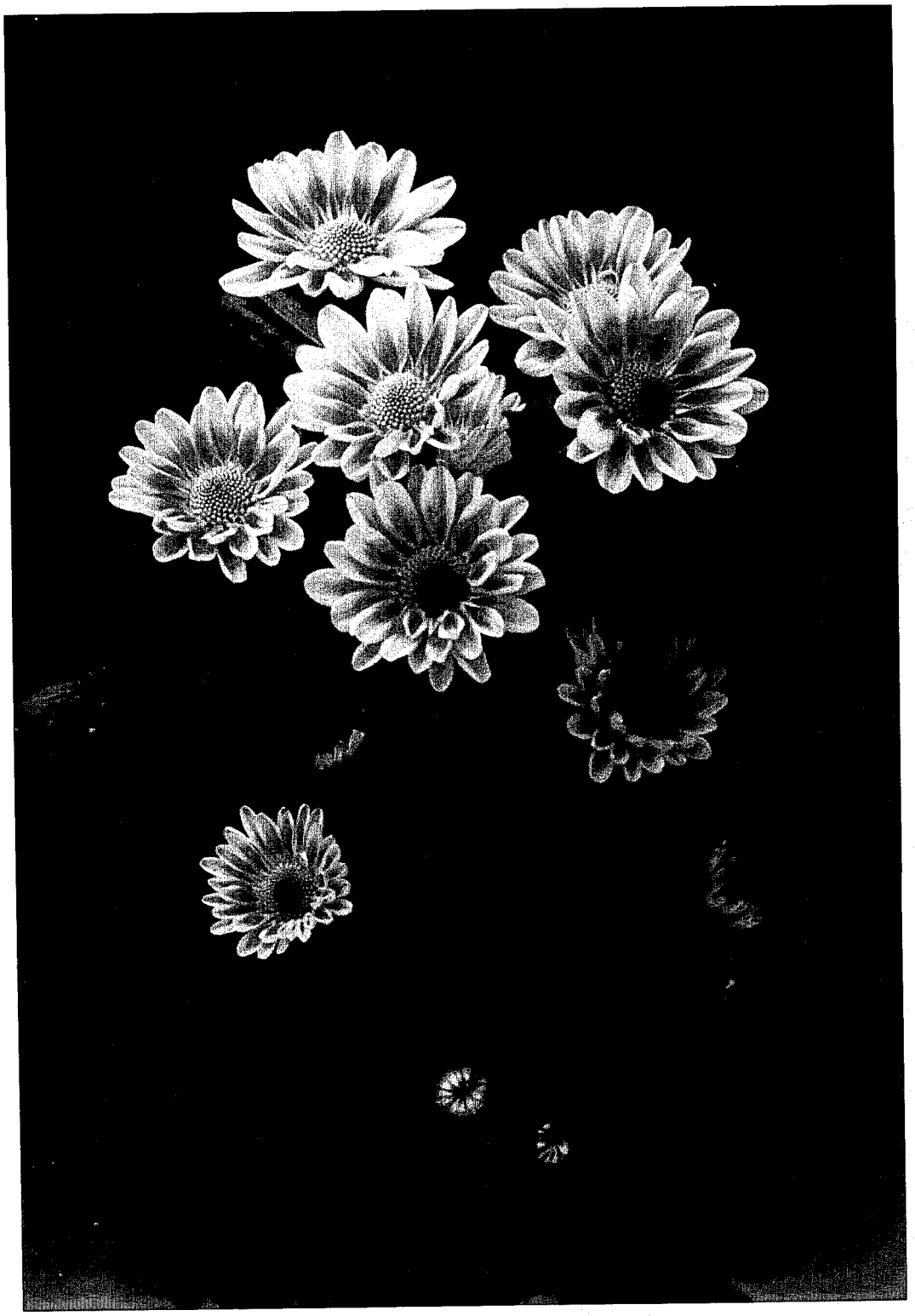

* * * * *